United States Patent [19]
Chun

[11] Patent Number: 5,555,797
[45] Date of Patent: Sep. 17, 1996

[54] CONTROL SYSTEM AND METHOD FOR A KIMCHI FERMENTOR

[75] Inventor: Jae K. Chun, Suweon, Rep. of Korea

[73] Assignee: SamSung Electronics Co., Ltd., Suwon, Rep. of Korea

[21] Appl. No.: 917,375

[22] Filed: Jul. 23, 1992

Related U.S. Application Data

[62] Division of Ser. No. 278,230, Nov. 30, 1988, Pat. No. 5,142,969.

[30] Foreign Application Priority Data

May 28, 1988 [KR] Rep. of Korea ............... 1988/6278

[51] Int. Cl.⁶ .................. C12H 1/00; A23B 4/00
[52] U.S. Cl. .................. 99/468; 99/470; 99/483; 99/486; 73/861.41; 426/49; 435/286.1; 435/289.1
[58] Field of Search .................. 99/276, 331, 451, 99/467, 468, 470, 472, 483, 486, 493, 506, 534, 535; 435/289, 290, 291, 313, 316; 426/49; 73/861.41

[56] References Cited

U.S. PATENT DOCUMENTS

| | | | |
|---|---|---|---|
| 2,333,791 | 11/1943 | Hutchison, Jr. | 73/861.41 |
| 2,967,450 | 1/1961 | Shields et al. . | |
| 3,295,994 | 1/1967 | Lee | 426/49 |
| 3,403,554 | 10/1968 | Chevlier et al. | 73/861.41 |
| 3,753,731 | 8/1973 | Christ | 99/472 |
| 3,809,618 | 5/1974 | Muller | 435/316 |
| 3,926,738 | 12/1975 | Wilson et al. . | |
| 3,978,918 | 9/1976 | Nagatomo et al. | 435/316 |
| 4,062,276 | 12/1977 | Stahmann | 99/467 |
| 4,204,037 | 5/1980 | Dill et al. | 435/290 |
| 4,293,655 | 10/1981 | Christ et al. | 99/472 |
| 4,315,990 | 2/1982 | Sheets | 435/289 |
| 4,318,992 | 3/1982 | Mila-de-la-Roca et al. | 435/291 |
| 4,692,414 | 9/1987 | Yamada et al. | 435/291 |
| 4,746,615 | 5/1988 | Buchholz et al. | 435/289 |
| 4,785,728 | 11/1988 | Miyata et al. | 99/535 |
| 5,240,721 | 8/1993 | Yun | 426/49 |

FOREIGN PATENT DOCUMENTS

| | | | |
|---|---|---|---|
| 1473083 | 11/1968 | Germany | 73/861.41 |
| 61-170337 | 8/1986 | Japan | 99/535 |
| 62-117514 | 5/1987 | Japan | 99/468 |
| 495534 | 3/1976 | U.S.S.R. | 73/861.41 |
| 640121 | 1/1979 | U.S.S.R. | 73/861.41 |
| 2032759 | 5/1980 | United Kingdom | 99/535 |

*Primary Examiner*—Stephen F. Gerrity
*Attorney, Agent, or Firm*—Robert E. Bushnell, Esq.

[57] ABSTRACT

A control system for a kimchi fermentor using a kimchi curing sensor constructed to detect gas bubbles and count the number of gas bubbles produced. For mass production of kimchi or other naturally fermenting foods, the control system includes a microprocessor for operating a heater, cooler, and agitator mounted in one or more kimchi barrels in response to a stored program. In another embodiment, the kimchi fermentor is adapted to a home refrigerator, controlling the compressor and fan of the refrigerator in lieu of said cooler and agitator. The microprocessor receives signals from the kimchi curing sensor and a temperatures sensor, and in response generates control signals to maintain a constant temperature until a desired degree of fermentation is reached, whereupon the microprocessor maintains a storage temperature. A fermentation mode is selectable by the user, and the microprocessor displays its current operation mode.

32 Claims, 8 Drawing Sheets

KIMUCHI FERMENTATION CURVE OBTAINED BY THE KIMUCHI CURING SENSOR PER HOUR

KIMUCHI FERMENTATION CURVE OBTAINED BY THE KIMUCHI CURING SENSOR PER 2 HOURS

Temperature Effects On The Kimuchi Fermentation Curve

Environmental Temperature Oscillation Effect On The Bubbles Counting Capability Of The Kimuchi Curing Sensor In Kimuchi Fermentation

CONTROL SYSTEM AND METHOD FOR A KIMCHI FERMENTOR

CROSS-REFERENCE TO RELATED APPLICATIONS

This is a divisional of Ser. No. 07/278,230, filed Nov. 30, 1988, now U.S. Pat. No. 5,142,969.

BACKGROUND OF THE INVENTOR

The present invention relates to a kimchi fermentor, and particularly to a kimchi fermentor and control system thereof using a kimchi curing sensor.

Kimchi is made of pickled vegetables including radish, cabbage and cucumber, and it is an indispensable dish in Korean cuisine. However there have been numerous problems in its mass production and mass storage until now, because kimchi is a naturally fermented food and fermented kimchi has the defect of acidifying itself at room temperature.

Due to these problems, it is difficult to properly cure and produce kimchi on a commercial scale. While the problem of preserving cured kimchi for long periods is well known, it can not be said that the unique taste of kimchi is truly preserved without controlling the fermentation for its curing. For example, with respect to the spread of refrigerator services for preserving kimchi, refrigerators have been used predominantly for preserving kimchi for long periods. But kimchi stored in refrigerators ferments even at relatively low temperatures. Also, kimchi produces a unique odor which greatly influences other foodstuffs stored with it. Therefore, kimchi has not been produced to have the right taste in a refrigerator.

In light of this, it is an innovation if kimchi can be easily prepared to have the right taste, and the right taste can be preserved for a long time. Therefore, it is desirable that kimchi have its degree of curing determined by means of a sensor, which can detect and measure the degree of curing based on physiology, and that kimchi can be stored while maintaining the right taste for a long period. Conventional methods for automatically preparing kimchi however, comprise only the steps of pickling kimchi, then controlling the fermentation period and temperature. Thus, undesirable results have been caused by the kimchi manufacturing process, the fermentation period and temperature, or the type of spice and the quantity of sauce. That is to say, kimchi is a product with a sour taste, due to the organic acid obtained when microorganisms increase in the pickled vegetable and the fermentation phenomenon occurs during kimchi curing. It is well known that the taste of kimchi is greatly influenced by the type of vegetable used, the type of the organism associated with kimchi, the salt concentration, and the temperature acting decisively to the increase of the number of microorganisms.

Therefore the design and construction of a kimchi fermentor must consider the fermentation physiology of kimchi. Also it has been an important task, in order to automatically manage the curing of kimchi, that optimum control variables be derived which correspond to the degree of curing. Previously, the kimchi fermentation characteristics reported in Korea and overseas are its acidity, or pH level. Thus the present invention aims at the design and construction of a kimchi fermentor, which uses the change in acidity pH as the measuring variables. However, installing acidity measuring equipment in a home refrigerator would be very expensive and not economical. Furthermore, even if an acidity sensor were used in a refrigerator, a standard buffer solution must be used which could contaminate the kimchi. Also, if the acidity electrode were accidentally broken, the mercury and silver which are the constituent parts could cause serious contamination. Therefore, it is very important that new variables be found which are capable of indicating kimchi curing. Furthermore the variable adapted to the automatic control of a kimchi fermentor must be easily convertible into a reliable electric signal. Thus, it is further desirable for a kimchi fermentor to have a variable which is economical to measure and provides a stable electric signal.

In order to find a variable adapted to kimchi curing, pressure changes relative to kimchi juice and the amount of gas produced during fermentation have been measured. That is, the representative physical change after preparing kimchi is to produce kimchi juice. Therefore it is known that changes in the amount of kimchi juice are easily measured and also are easily converted into electric signals. It has been proven, however, that the change in the amount of juice is caused by the protoplasm separation phenomenon and is in equilibrium sooner, whereas the amount of kimchi juice formed under various artificial temperatures and conditions have not for the most part been influenced by the degree of temperature. Thus, it is well known that the change in the amount of juice cannot be used as a variable representing the beginning of kimchi curing or of the fermenting status.

In connection with the amount of the gas generated while fermenting kimchi, it has been published that kimchi curing is closely related to the activities of microorganisms but is independent of acidity. Substantial kimchi fermentation mechanism makes the group of the anaerobic or facultative microorganism, including Lactobacillus plantarum, which dissimilate the vegetables directly or the microorganism increases in the basic dissoluable filtered solution to produce organic acid and $CO_2$. At that time, the concentration of the organic acid represents the acidity, which had been broadly used as the index of kimchi curing. Thus it is found that if a method is developed for effectively measuring the amount of a gas produced, such as $CO_2$, it has the high possibility of practical application as an index of kimchi curing, much the same as the acidity value commonly used. Specifically, gas measurement is more easily performed than acidity measurement, and the cost for constructing gas measuring apparatus is low.

Accordingly, a pressure cell was used to measure the amount of gas produced by fermenting kimchi, in which a kimchi sample was put in the pressure cell and then the pressure cell inserted into a case having kimchi to be fermented. Herein it is noted that the pressure cell has a capillary tube connected to a transducer, which measures the pressure and converts the pressure into an electrical signal. Therefore the pressure produced in the pressure cell was measured through the capillary tube at the transducer. As a result, it was experimentally confirmed that the pressure in the cell represented a curve similar to that of the microorganism increase, but after the lapse of 24 hours time the pressure in the cell had not further changed. During this experiment, kimchi had its acidic taste when the pressure in the cell was at the highest level. Its taste was equal to that of kimchi when the $CO_2$ gas is produced in the largest quantity.

Therefore it has been proven that a pressure cell can be used as the sensor for measuring kimchi curing, but the reproducabilty of the measurement must be proven in order for it to be useful as sensor. As to it, it had been observed whether the amount of kimchi sampled from the prepared kimchi is fermented in the sensor cell and which prepared kimchi is put in a kimchi case along with the sensor cell. As a result, it has been found that since the fermentation of kimchi is not relative to true cultivation but to natural increasement, the growth aspects of the bacterium differ between kimchi in a case and kimchi samples in the kimchi sensor was developed in accordance with the lapse of the fermenting time even though the same samples were used at the time being intended to prepare kimchi. That is, because the growth environment of the bacterium in the pressure cell is different from the growth environment of the bacterium in the kimchi case, the possibility for inhibiting the growth was overlooked. Thus the pressure cell does not have the same reproducability as the sensor for sensing kimchi curing.

In the procedures of these studies, it has been found that kimchi induces generation of gas during fermentation. The gas generated as the product of the basic disassimilating metabolism and the respiration of the microorganism is dissolved in part in the kimchi solution but is mostly discharged out of the kimchi solution forming a gas bubble. It has been observed that the generation of gas bubbles usually does not occur at the beginning of fermentation, when the concentration of the bacterium is relatively lower. Upon reaching the logarithmic growth phase, however, gas bubbles are significantly increased in size and number and become capable of being seen with the naked eye. The present invention requires apparatus which can collect the gas in an open kimchi case, in order to overcome the disadvantages causing the failure of the control system due to air exposure of the kimchi case due to less than perfect sealing of the pressure cell.

Considering these points, it should be noted that the sensor for sensing kimchi curing may have variables according to the kimchi preparing, if the sensor has the reproducability and senses the curing degree of kimchi under various temperatures and conditions. Thus if this kimchi curing sensor is developed, a kimchi fermentor is easily constructed. Also a kimchi fermentor must be easily controllable on the basis of the variables obtained from the kimchi curing sensor. Since the kimchi fermentor is designed or configured on the basis of the fermenting process, the fermenting procedure must be accurately measured, and kimchi fermenting status and environment must be controlled before executing the design of the refrigerator. Also the design of a kimchi fermentor must consider the growth characteristics of the microorganism, including physiological characteristics, and the mechanical and electronic characteristics of the control system, as a single system. For example, it takes about one week to complete the procedures comprising the steps of pickling kimchi and curing it through fermentation. Further kimchi fermentation must be accompanied through reiterated experiments because it is not a true cultivation which has its properly configured method relative to the automatic fermenting system of kimchi. Therefore the fermenting control system of kimchi must comprise all parts substantially required for the design of a kimchi fermentor as well as the measuring and controlling systems.

SUMMARY OF THE INVENTION

In light of this, the primary object of the present invention is to provide a new sensor for sensing the degree of kimchi curing in the control system and converting that information into an electric signal.

Another object of the present invention is to provide a kimchi fermentor including a heating device and a cooling device to control kimchi fermentation, and an agitator for balancing the temperature in a kimchi case, in view of the fact that kimchi curing is largely influenced by the increase of the microorganisms and that the growth of the microorganisms is influenced by the cultivation temperature.

Another object of the present invention is to provide a control system for independently controlling a heater, cooler and agitator so that a constant temperature is maintained within an error range of plus or minus ($\pm$)0.5° C. relative to various temperature ranges and such temperature range can be programmed.

These and other objects may be accordingly obtained with a kimchi curing sensor constructed according to the principles of the present invention comprising the following:

An easily constructed gas bubble collecting apparatus made of plastic, in order to prevent deterioration caused by extended contacting with kimchi.

A gas bubble homogenizing apparatus, made from a material capable of facilitating movement of the gas bubbles from the collecting means, in the form of the tube having a diameter of within the range of 5 to 8 millimeters.

A measuring circuit for counting the number of the gas bubbles, including a photo interrupter and a binary counter for counting the frequency of the interruptions detected by the photo interrupter.

Also the kimchi fermentor constructed according to the principles of the present invention can use a conventional refrigerator by establishing the standardization of other conditions except for the temperature with respect to kimchi samples in view of the fact that kimchi fermentation is considered a natural fermentation, and the present invention comprises the following components.

At least one kimchi case having the curing sensor which is installed in the refrigerator to control kimchi curing, At least one fermenting barrel including a heating means, an agitating means and cooling coils for controlling the temperature therein, A kimchi curing fermenting control system for controlling kimchi fermentation in accordance with a signal from a temperature sensor in the barrel and a kimchi curing sensor, A cooling means and a number of relays for controlling the operation of the heating means and the cooling coils in accordance with control signals from the control system.

Also, a kimchi curing fermenting control system of the present invention comprises the following;

A microcomputer for detecting the degree of kimchi curing in accordance with kimchi fermenting and forcing the cured kimchi to store in a refrigerated state, An operating portion for operating the compressor and fan motor of a refrigerator, and a heating means according to the present invention, A controlling portion for controlling the operating portion, A kimchi curing sensing portion for receiving a sensing signal from a kimchi curing sensor and inputting a square wave to the microcomputer, A temperature sensing portion for convening into a digital signal an analog signal generated by a temperature sensor installed in a fermenting barrel in accordance with the predetermined temperature, A displaying portion for showing the operation mode of the kimchi fermenting controlling system in accordance with a degree of curing.

The present invention is operated in accordance with the following kimchi preparing method.

Performing the initialization work to adjust the fermentation level selected by the key input and selecting the corresponding function, Judging what mode is operated among the strong mode, the middle mode and the weak mode of the fermentation control based on whether the temperature set through the fermentation selection is higher than the predetermined temperature and displaying the fermenting level relative with the fermenting states on the outside following turning on the heating means, Counting the gas bubbles and adjusting the temperature of the refrigerator to a predetermined fermentation temperature if a predetermined fermentation time has not elapsed, Judging whether the number of gas bubbles divided by the predetermined time is larger than that of the gas bubbles counted before the predetermined times, if the fermentation times is lapped over the predetermined times.

Storing the number of gas bubbles counted so far in the memory if the number of the gas bubble is larger than that of the predetermined number and adjusting the temperature of the refrigerator to the predetermined temperature, Performing the weak mode of fermentation when the second peak point of gas bubbles appears, or the standard mode when the peak point of gas bubbles appears thirdly, based on what times the peak states of gas bubbles occur if the number of gas bubbles is smaller than that of the gas bubble, and cancelling the fermentation function under the standardization mode of the fermentation.

And at the last step the kimchi is stored under refrigerated conditions.

BRIEF DESCRIPTION OF THE DRAWINGS

A more complete appreciation of this invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION

Figure 1:
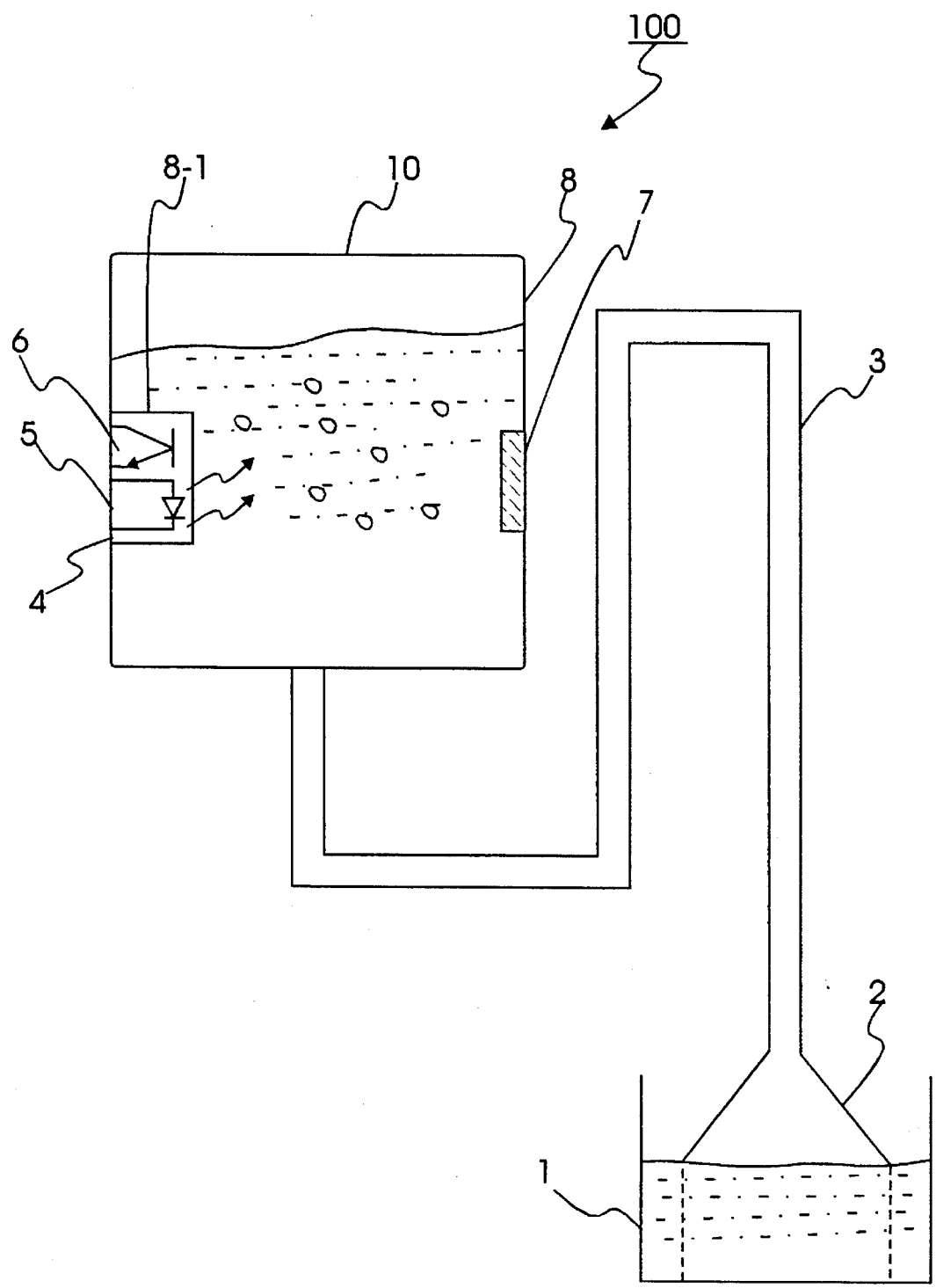
FIG. 1 is a schematic view representing the kimchi curing sensor according to the present invention.

Turning now to the drawings, FIG.1 shows kimchi curing sensor 100 of the present invention. Kimchi curing sensor 100 comprises a binary counter (not shown), gas collecting portion 2, gas bubble homogenizing portion 3, case structure 8, and gas bubble measuring portion 10. The gas bubble collecting portion is made of plastic in the form of a funnel over kimchi case 1. Gas bubble homogenizing portion 2 is made of tetraflouroethylene (TFE), commonly known by the trademark Teflon®, to transfer the gas bubble therein and render the size of the gas bubble. Case structure 8 is in the form of a box having its lower portion coupled to gas bubble collecting portion 2, which is the transferring tube of the gas bubble and receives the transparent liquid solution up to a predetermined height therein. Transparent case 8-1 is sealingly mounted to one wall of case structure 8, and is provided with a photo interrupter 4 including a photo diode 5 and photo transistor 6 therein. A reflecting film 7, such as silver paper, is attached to the wall opposite said transparent case. Though not shown in the drawing, the binary counter is connected to photo interrupter 4 and gas bubble measuring portion 10 is connected to a microcomputer (not shown).

Figure 2A:
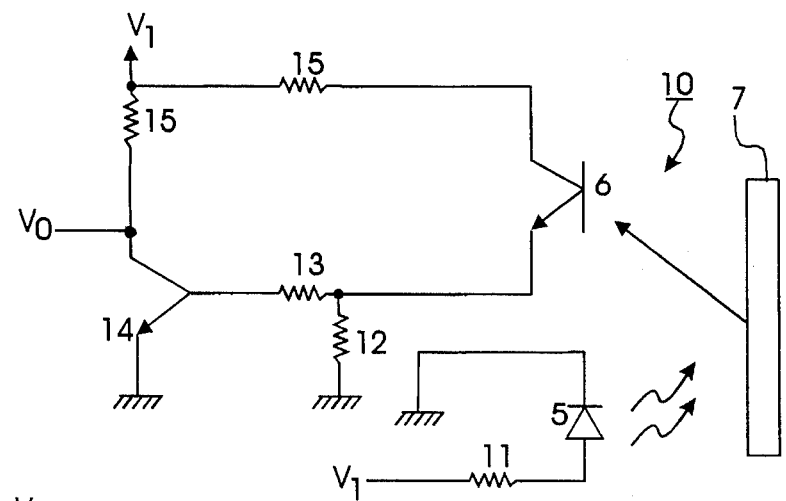
FIGS. 2A, 2B, 3A and 3B are schematic views representing the operation principle of the kimchi curing sensor according to the present invention.
Figure 2B:
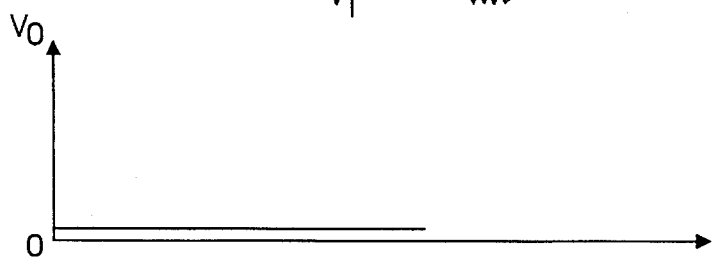

Gas bubble measuring portion 10 and its operational characteristics are shown in FIGS. 2A, 2B and FIGS. 3A, 3B. Photo interrupter 4 is operated when power source $V_1$ is applied though resistor 11 to photo diode 5. Photo diode 5 is lit, and if the light is reflected by reflecting film 7, photo transistor 6 receives the reflected light. At this time photo transistor 6 is triggered so that power source $V_1$ is applied through resistor 15 to the base of transistor 14 by way of resistors 13 and 12. Transistor 14 is triggered to output power source voltage $V_0$ through resistor 16. This voltage represents the non-detecting status of the circuit as shown in FIG. 2b. In other words, due to the operation of transistor 14, power source voltage $V_0$ is grounded.

Figure 3A:
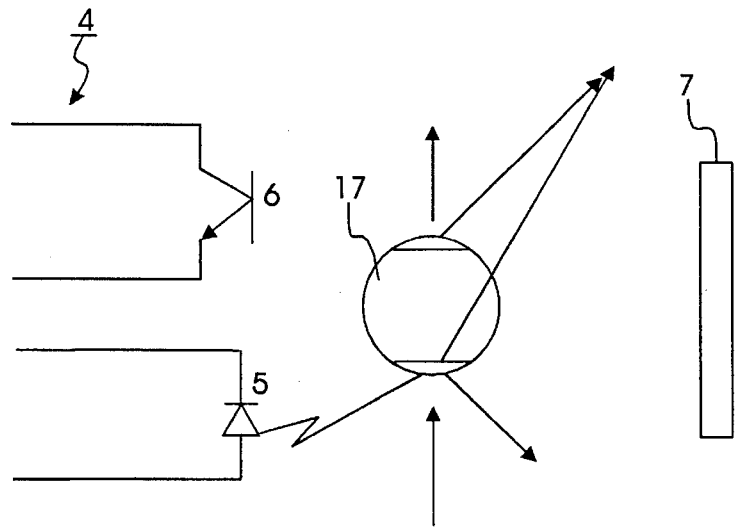
Figure 3B:
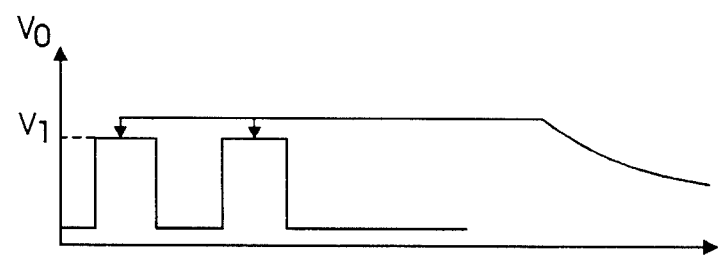

As shown in FIG. 3A, the light of photo diode 5 is diffused by gas bubble 17 when the gas bubble is produced, so that the light does not reach photo transistor 6. Photo interrupter 4 is not operated since the light diffused by gas bubble 17 is not applied to photo transistor 6. Accordingly, measuring portion 10 produces a pulse signal, whereby power source $V_1$ is dropped by means of resistor 16 to output voltage $V_0$ when a photo transistor 6 is screened by a gas bubble, but is reduced to ground potential when photo transistor 6 is not screened by gas bubble 17, as shown in FIG. 3B.

Therefore, it is understood that kimchi curing sensor 100 helps to easily measure the amount of gas bubbles produced during kimchi fermentation and obtain the following results.

Figure 9:
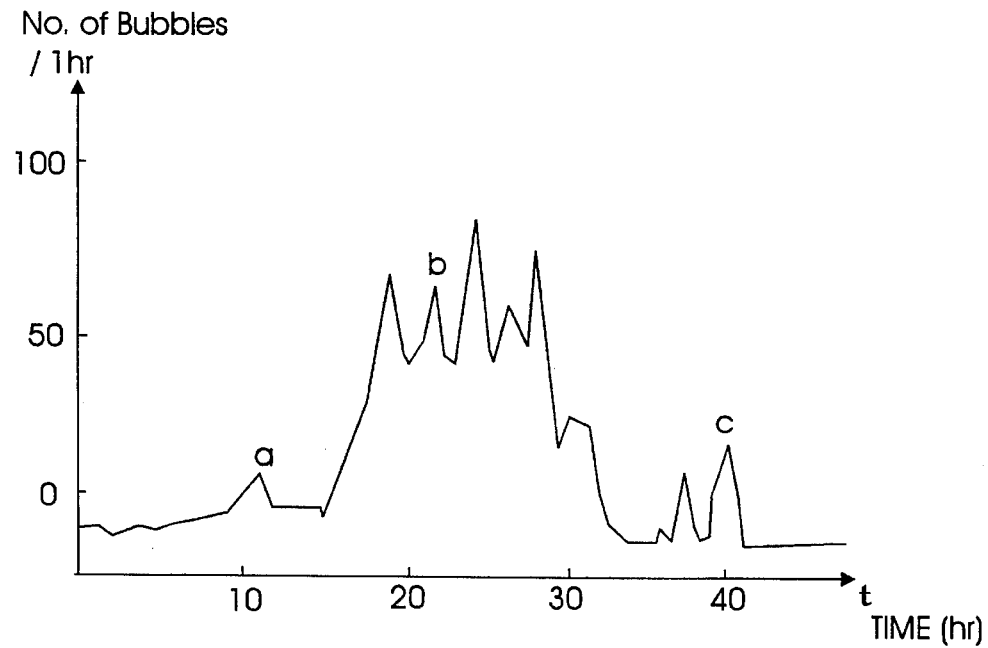
FIG. 9 is a graph representing the number of the gas bubbles formed by the kimchi curing sensor per one hour.
Figure 10:
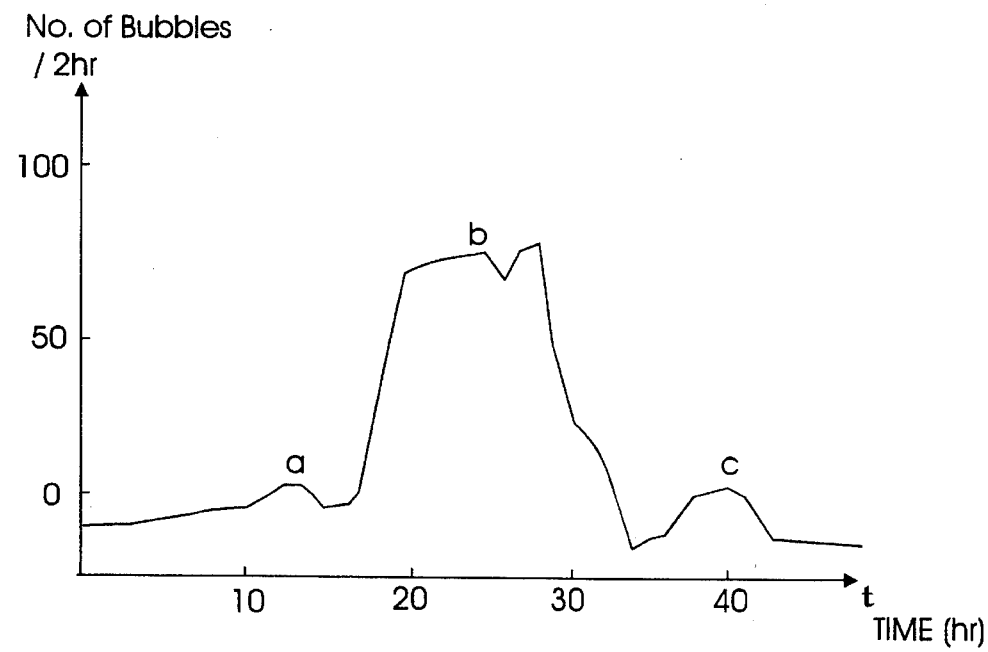
FIG. 10 is a graph representing the number of the gas bubbles formed by the kimchi curing sensor per two hours.

The specific kimchi curing curves in FIG. 9 and FIG. 10 may be obtained, showing the rate of gas bubble production as the number of the gas bubbles produced in a predetermined period versus the elapsed fermenting time, when kimchi curing sensor 100 is mounted on a kimchi case having kimchi fermented at 25° C., in order to test the capacity of kimchi curing sensor 100 during fermentation. FIG. 9 is a curve drawn on the basis of the number of gas bubbles produced per hour, and FIG. 10 is a curve drawn on the basis of the number of the gas bubble produced every two hours.

As shown in the drawings, it is noted that some peak points have appeared. In connection with FIG. 10, it is seen that the curve of gas bubbles production rate drawn every two hours represents kimchi fermentation characteristics superior to those in FIG. 9. For example, the relatively lower peak 'a' at the beginning of fermentation represents the starting of fermentation, and after twenty-four hours the main peak 'b' appears, when the main fermentation is prosperously occurring. When the sampling period over which the gas bubbles are counted is relatively shorter, the rate curve has a very irregular aspect (FIG. 9), but when the sampling period is relatively longer, the rate curve shows a regular aspect (FIG. 10). Herein the first peak point 'a' is the starting point of kimchi curing, the second peak point 'b' represents the prosperous curing of kimchi, and the third peak point 'c' is the last step, which indicates that kimchi fermentation is complete.

Figure 11:
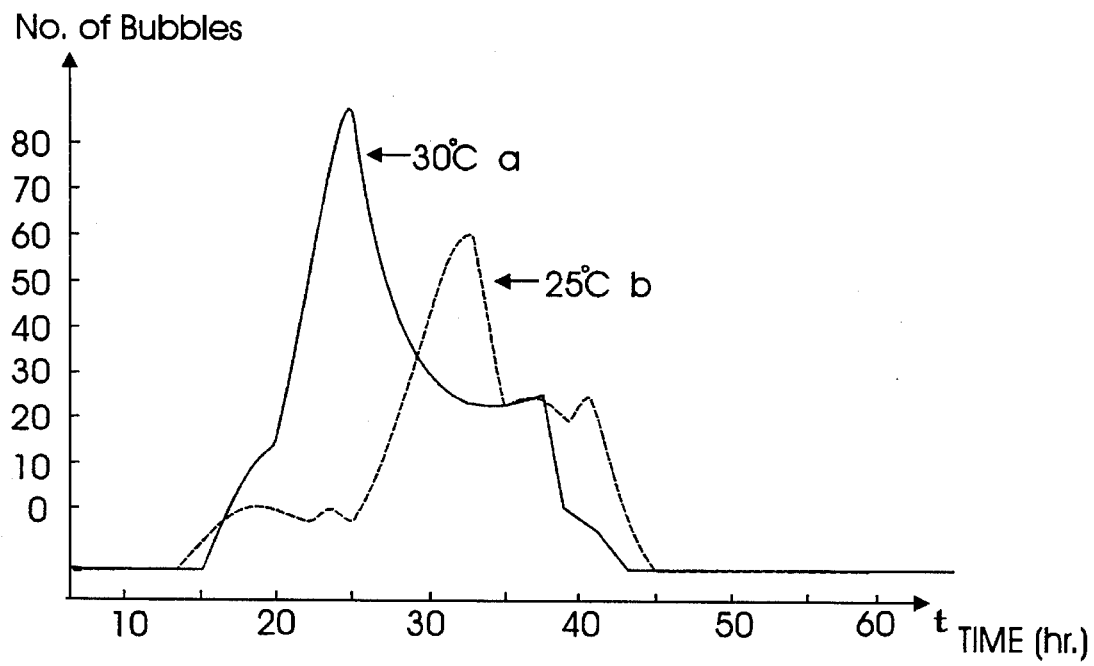
FIG. 11 is a graph representing the effect of temperature at both 30 C. and 25 C. with respect to the kimchi fermentation curve.

On the other hand, when the gas production rate under various kimchi fermentation temperatures is investigated, the curve as shown in FIG. 11 may be obtained, in which the fermentation temperature is 25° C. and then 30° C. These curve forms are similar to each other even in any test method, but it is known that the higher the temperature becomes, the earlier the peak points representing the beginning of fermentation and the period of the main fermentation appear. Such results reflect the normal tendency that increased temperature accelerates fermentation.

Figure 12:
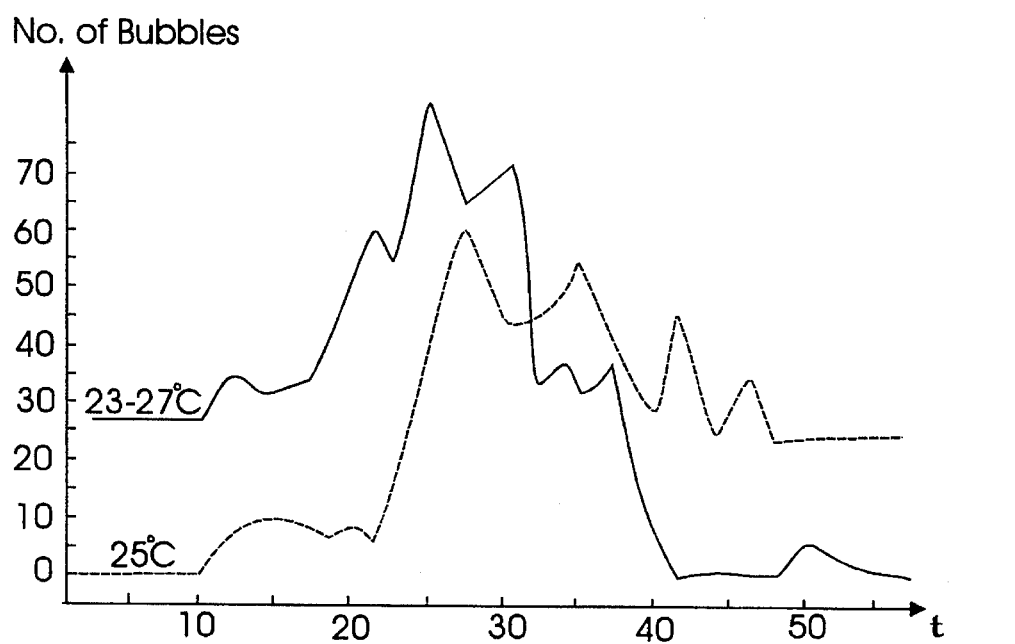
FIG. 12 is a graph representing the circumferential temperature effect with respect to the count of gas bubbles obtained by kimchi curing sensor during fermentation.

Also, as shown in FIG. 12, it may be useful to test the capacity for measuring gas bubbles under changing environmental condition prior to use of the kimchi curing sensor in a kimchi fermentor or refrigerator, and to sense kimchi curing under these conditions. In order to accomplish these objects, the kimchi fermenting control system of the present invention is equipped with a program which controls the temperature while kimchi is fermented in a barrel within plus or minus (±)2° C. by turning said system on or off. When kimchi curing sensor 100 is mounted on the barrel, the signal measuring the gas bubble production rate is shown in FIG. 12. That is, the curve showing the dotted line in the drawing represents the result at a constant temperature of 25° C. and the solid curve in the drawing represents the result under temperature changes between 23° and 27° C. It certifies that the kimchi curing sensor of the present invention is adequate when used under the temperature environment of a refrigerator changing in the range of 2 to 3° C. Accordingly, the present invention can use a conventional refrigerator. Therefore it is needed for constructing refrigerators in which the new kimchi fermenting barrel is to be installed, because it is necessary to adjust the kimchi curing temperature in light of the fact that kimchi is a naturally fermenting food and it is very important to maintain the same environmental condition except for the temperature.

Figure 4:
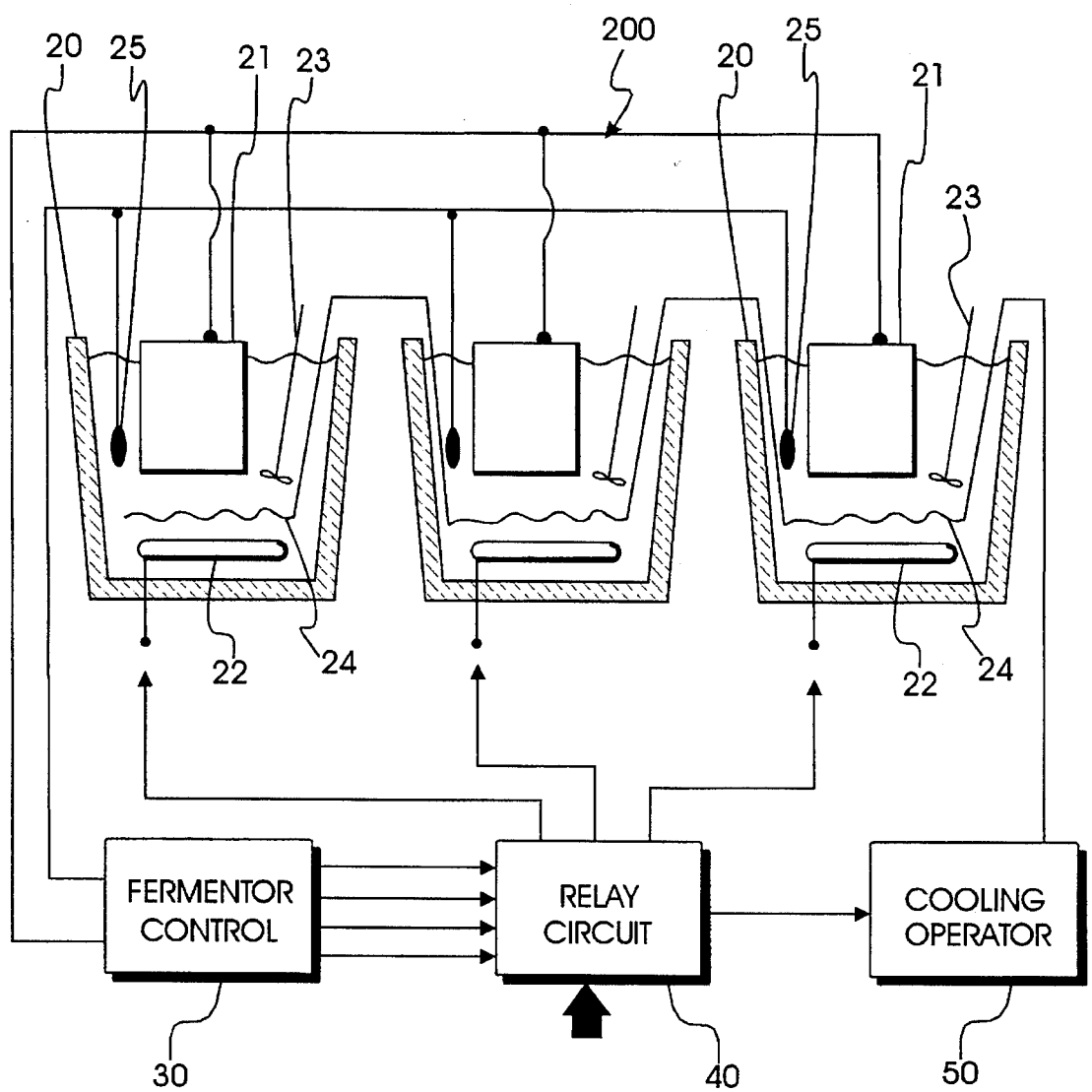
FIG. 4 is a view representing a kimchi fermentor according to the present invention.

For this reason, the fermentor of the present invention is provided with kimchi fermenting barrel 20 which maintains the same fermenting conditions except for the temperature. As shown in FIG. 4, kimchi fermenting barrel 20 is provided with a kimchi case 21, into which kimchi is put, and kimchi curing sensor 100 (not shown) is installed. Heater 22 controls kimchi fermentation. Also, agitator 23 is mounted near the inner peripheral wall of kimchi case 21 to uniformly transfer the temperature around the wall. Cooling coil 24 is mounted in kimchi fermenting barrel 20 to cool the kimchi in kimchi case 21 in order to change to a storage mode when the kimchi is completely cured. Temperature sensor 25 is installed in the kimchi fermenting barrel to detect the temperature therein. Kimchi curing fermentor control 30 receives the fermenting signal from kimchi curing sensor 100 and the temperature signal from temperature sensor 25 so that it controls relay operating portion 40 to operate heater 22 or cooling operating portion 50. It will be understood that kimchi s fermentor 200 is provided with at least one kimchi fermenting barrel for the mass production of kimchi.

Figure 5:
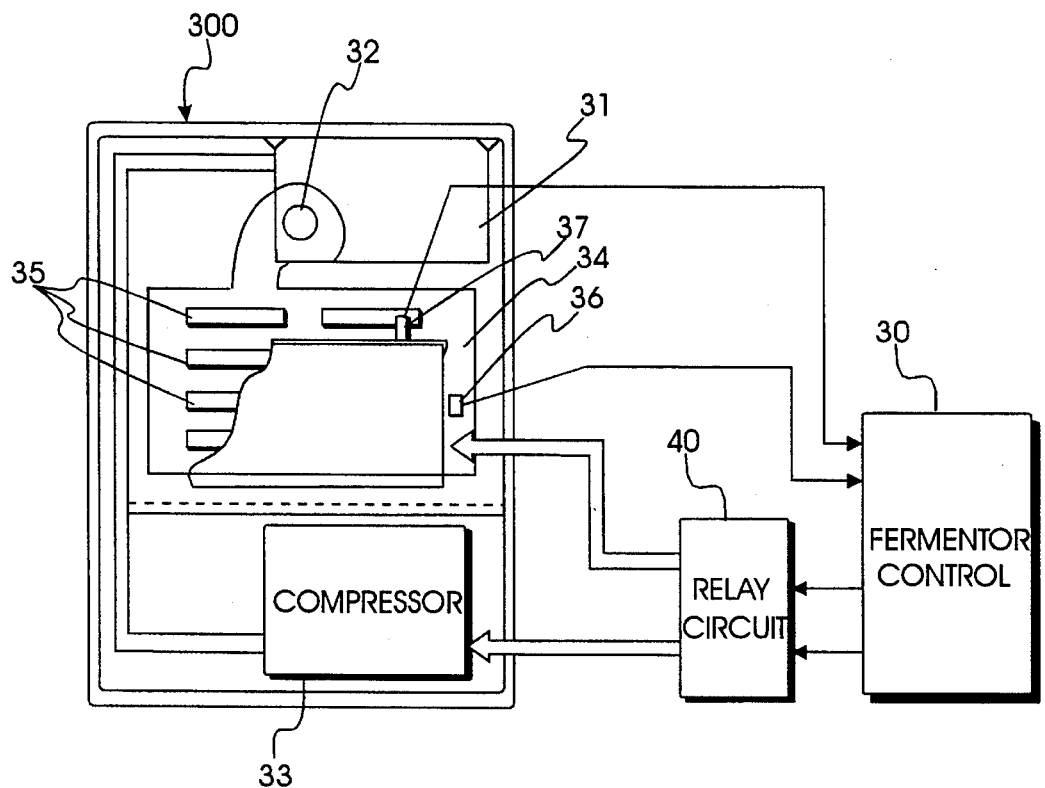
FIG. 5 and FIGS. 6A and 6B are respectively a cross-sectional view, a front view, and a side view representing the embodiment in which the kimchi fermentor of the present invention is adapted to a refrigerator.
Figures 6A, 6B:
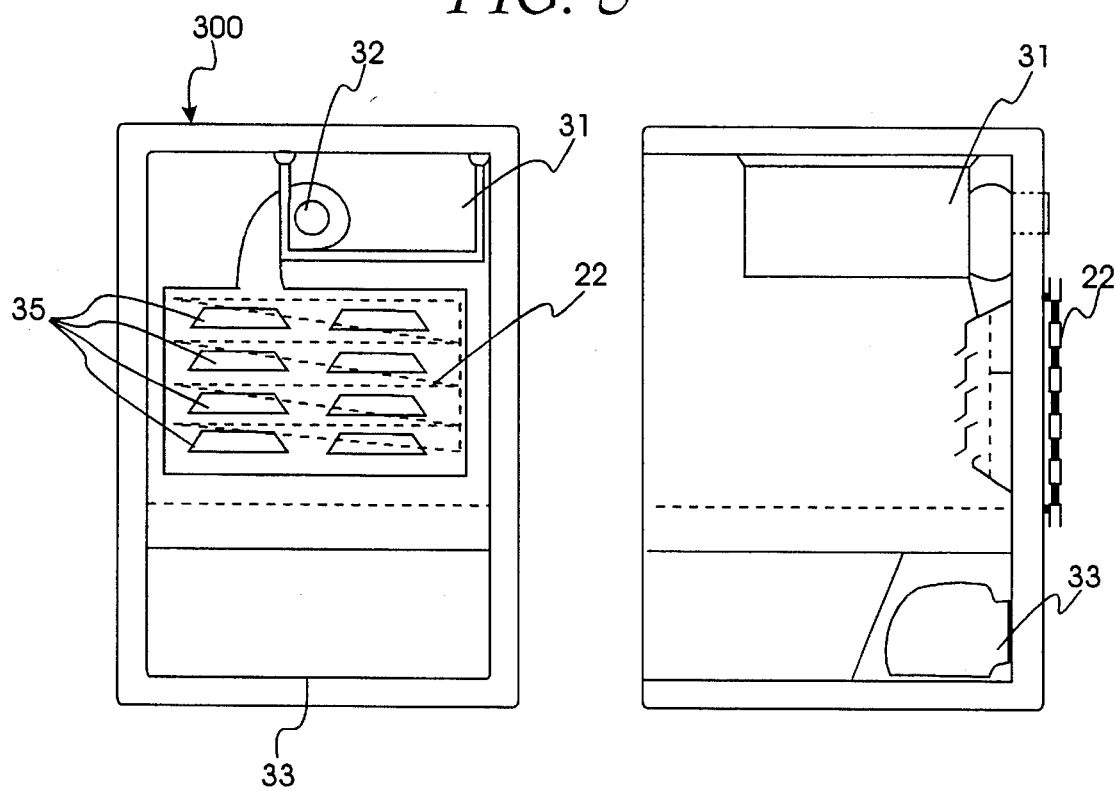

According to a second embodiment, shown in FIG. 5 and FIGS. 6A and 6B, if the kimchi fermentor of the present invention is adapted to a home refrigerator, refrigerator 300 is provided in a conventional configuration, with evaporator 31 in an upper portion, a fan 32 mounted adjacent to evaporator 31, and a compressor 33 in a lower portion connected to operate with evaporator 31. A number of kimchi cases 35 are properly arranged in refrigerating chamber 34 along with temperature sensor 36 and kimchi curing sensor 37. Herein kimchi curing sensor 37 may be mounted in a number of kimchi cases 35, or at the outside of refrigerating chamber 31. Also heater 22 is mounted on the rear portion of kimchi case 35 in refrigerating chamber 31 as shown in FIGS. 6A and 6B, or into the inner portion of the kimchi cases 35, respectively. Therefore it can be seen that a fan 32 and evaporator 31 of a home refrigerator may perform the operation of temperature equilibrium in lieu of the agitator 23 and cooler 24 shown in FIG. 4. The signal from temperature sensor 36 and kimchi curing sensor 37 is applied to kimchi fermentor control portion 30 similar to the device of FIG. 4. Relay operating portion 40 is operated according to signals from kimchi fermentor control portion 30, configured so as to control Compressor 33, fan 32 and evaporator 31. Accordingly, kimchi fermentors 200 and 300 of similar configurations are controlled by a kimchi fermentor control system 30, such as shown in FIG. 7.

Figure 7:
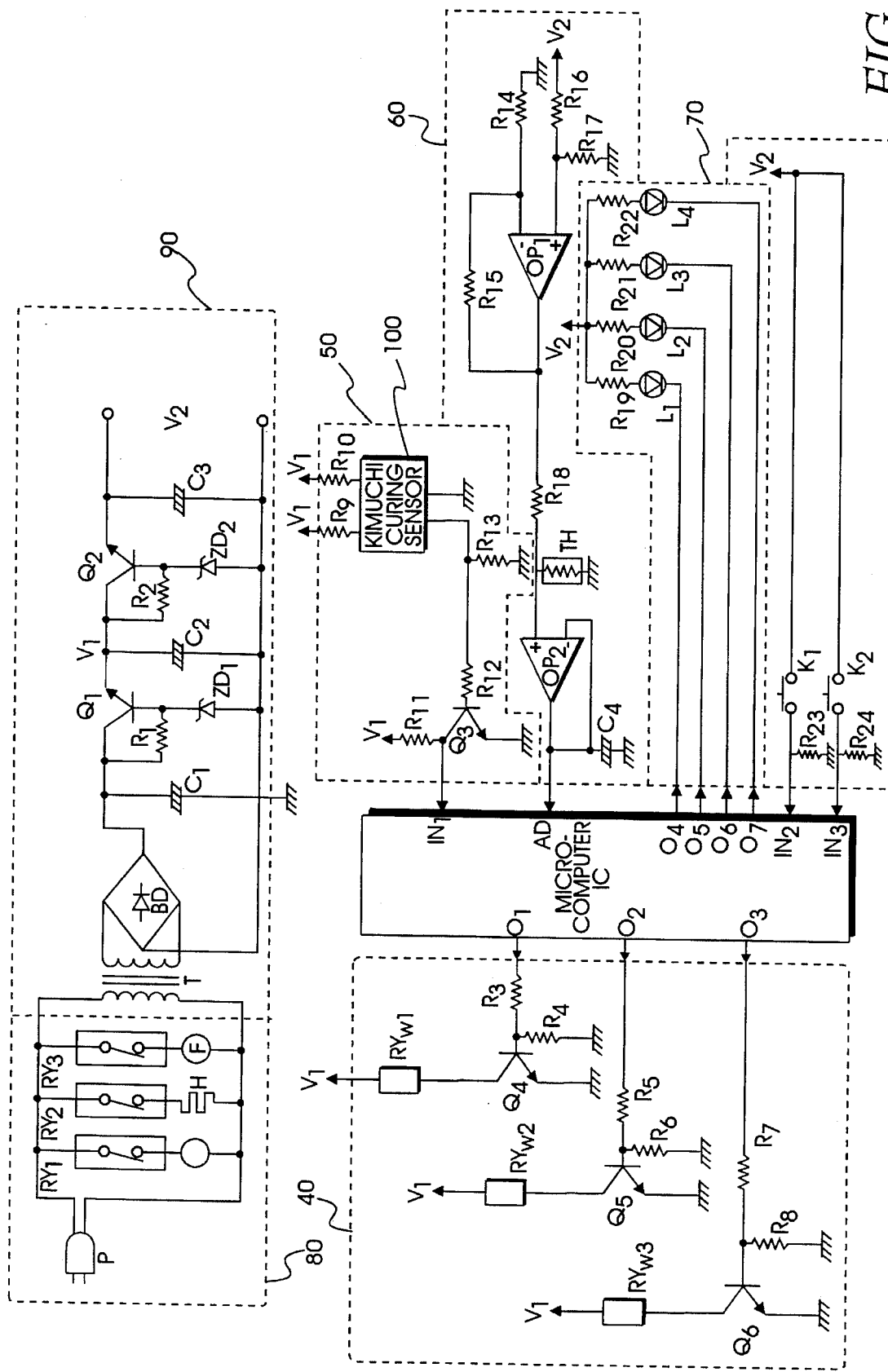
FIG. 7 is a detailed circuit representing the control system according to the present invention.

In FIG. 7, the kimchi fermentor control system comprises microcomputer $IC_1$ having input terminals $IN_2$ and $IN_3$, connected in pull down form by means of resistors $R_{23}$ and $R_{24}$ to key switches $K_1$ and $K_2$, respectively, for initializing the microcomputer. Kimchi curing sensing portion 50 is connected to inputting terminal $IN_1$ of microcomputer $IC_1$. Kimchi curing sensing portion 50 is provided with kimchi curing sensor 100 connected to resistors $R_9$ and $R_{10}$ that receive the power source voltage $V_1$. The output from sensor 100 is applied through resistors $R_{12}$ and $R_{13}$ to the base of transistor $Q_3$. Transistor $Q_3$ has the emitter grounded, and the collector connected through resistor $R_{11}$ to power source $V_1$ and is connected directly to input terminal $IN_1$, so that the signal like the pulse wave of FIG. 3A from kimchi curing sensor 100 according to the production of gas bubbles is applied to make microcomputer $IC_1$ count the pulses. Temperature sensing portion 60 is connected to analog to digital (A/D) terminal AD. This temperature sensing portion 60 is provided with operational amplifier $OP_1$ for producing the reference voltage. The noninverting terminal of operational amplifier $OP_1$ is connected through resistors $R_{17}$ and $R_{16}$ to power source $V_2$ and the inverting terminal of operational amplifier $OP_1$ is connected through resistor $R_{14}$ to the ground and through resistor $R_{15}$ in feedback form to the output terminal of operational amplifier $OP_1$. The reference voltage of operational amplifier $OP_1$ is applied through resistor $R_{18}$ to the non-inverting terminal of operational amplifier $OP_2$, in which resistor $R_{18}$ is connected in parallel to temperature sensor TH of a thermistor, and the output voltage from operational amplifier $OP_1$ increases or decreases according to the sensing states of temperature sensor TH. Operational amplifier $OP_2$ has the non-inverting terminal connected in feedback form to its output terminal and through condenser $C_1$ to ground, so that the sensing signal from temperature sensor TH is input to analog/digital terminal AD so as to measure the temperature in the fermenting barrel of a kimchi fermentor or the refrigerating chamber of the refrigerator.

Display portion 70 comprises light emitting diodes $L_1$–$L_4$ connected to output terminal $0_4$–$0_7$ of microcomputer $IC_1$, the other end of which is connected through resistors $R_{19}$–$R_{22}$ to power source $V_2$. Thus, each of the light emitting diodes $L_1$–$L_4$ displays the operation states of strong mode, weak mode, standard mode, or the storing mode in kimchi fermenting.

Relays operating portion 40 includes relay windings $RY_{w1}$, $RY_{w2}$ and $RY_{w3}$, each of which can apply the power source to the compressor, the heater and the fan, respectively by electromagnetically operating a corresponding relay solenoid $RY_1$, $RY_2$, and $RY_3$ shown in portion 80. These relay windings $RY_{w1}$, $RY_{w2}$ and $RY_{w3}$ respectively have on source $V_1$ and the other end connected to each of the collectors of transistor $Q_4$, $Q_5$ and $Q_6$. Transistors $Q_4$, $Q_5$ and $Q_6$ have their bases connected through resistors $R_3$, $R_4$, $R_5$, $R_6$, $R_7$, and $R_8$ to outputs $0_1$, $0_2$ and $0_3$ of microcomputer $IC_1$, respectively, and their emitters connected to ground. Thus, relay windings $RY_{w1}$, $RY_{w2}$ and $RY_{w3}$ are operated according to the controls of microcomputer $IC_1$ and relays $RY_1$, $RY_2$ and $RY_3$ are coupled so as to control the operation of compressor COMP, heater H and fan F connected in parallel to the primary winding portion of transformer T.

Power source portion 90 includes transformer T, the second winding portion of which is connected to bridge diode circuit BD. The output terminal of bridge diode circuit BD is connected to smoothing condenser $C_1$, at the back portion of which a constant voltage circuit is created. For example, the collector of transistor $Q_1$ is connected to bridge diode circuit BD, resistor $R_1$ is connected between the collector and emitter of transistor $Q_1$, and the base of transistor $Q_1$ is connected to zener diode $ZD_1$, the cathode of which is grounded. Thus, transistor $Q_1$ outputs the power source voltage $V_1$.

At the back portion of power source $V_1$ connected to smoothing condenser $C_2$, the constant voltage circuit with respect to the power source $V_2$ is constructed, in which the collector of transistor $Q_2$ is connected to the emitter of transistor $Q_1$, resistor $R_2$ is connected between the base and collector of transistor $Q_2$, and zener diode $ZD_2$ is connected to the base of transistor $Q_2$. Thus transistor $Q_2$ outputs the power source voltage $V_2$ through smoothing capacitor (i.e., condenser) $C_3$.

Figure 8:
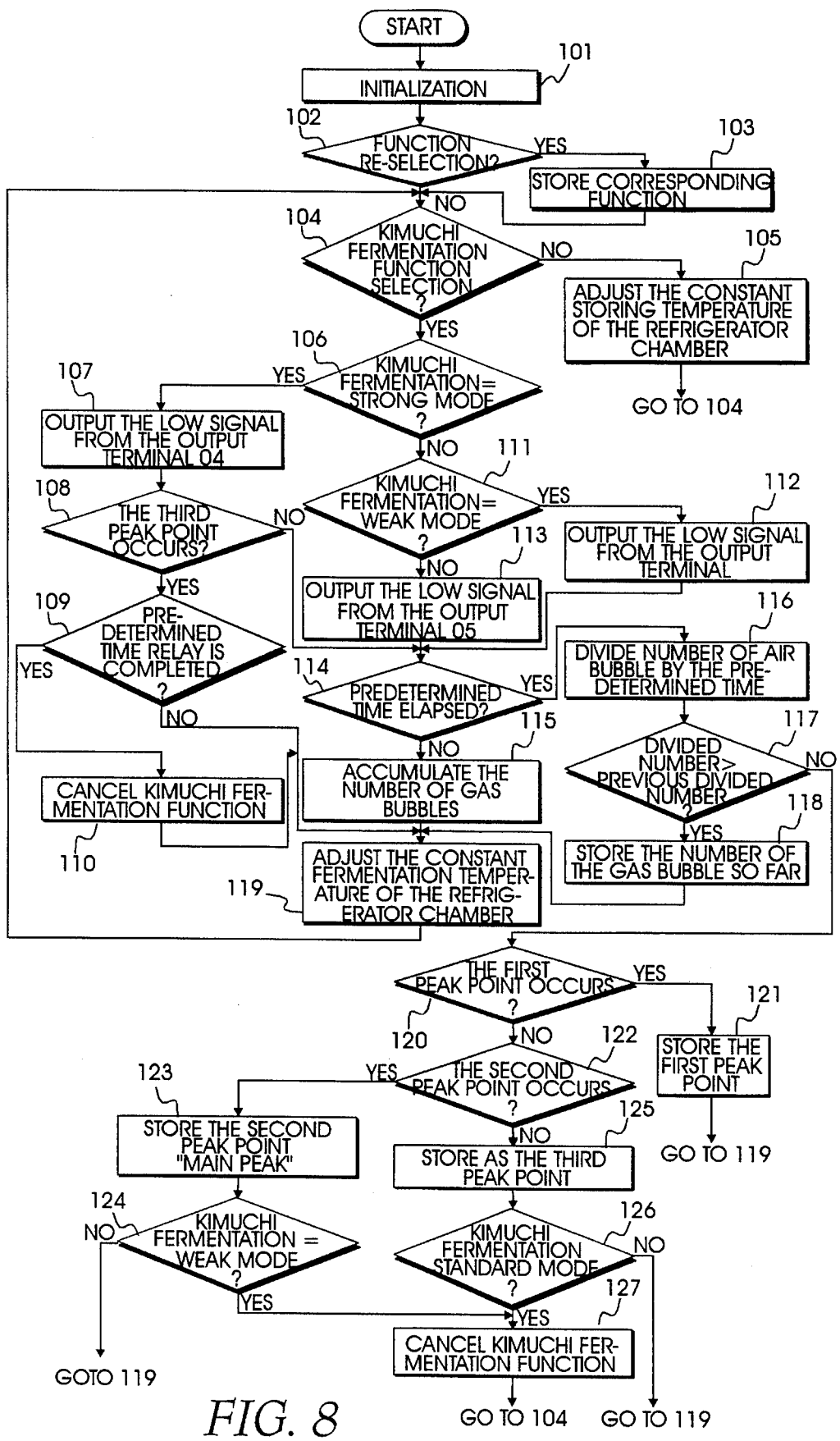
FIG. 8 is a flow chart representing the control method of the kimchi fermentor according to the present invention.

Referring now to FIG. 8, fermenting control system 30 of the present invention as described above first initializes microcomputer $IC_1$ in order to control the fermenting function of a kimchi fermentor according to the signal from kimchi curing sensor 100 (step 101). After initialization, at step 102 it is determined whether a particular system function has been selected, and if so, the corresponding function is stored in the memory (step 103). On the other hand, if no function selection was executed, step 102 goes directly to step 104 to judge whether the fermenting function is selected. If the fermenting function is not selected, the temperature in the refrigerating chamber is adjusted to a predetermined temperature (step 105). If the fermenting function is selected, step 104 goes to step 106 to judge whether the fermenting function was selected to operate at the strong mode.

If the kimchi fermenting selection is the strong mode, microcomputer $IC_1$ outputs a low level signal from its terminal $0_4$ (step 107). Thereafter at step 108 it is judged whether the signal from kimchi curing sensor 100 is considered the third peak point. If the signal is not indicative of the third peak point, step 108 moves to step 114 to continue fermentation. But in case of reaching the third peak point, at step 109 microcomputer $IC_1$ counts a predetermined delay time to identify the status of the third peak point and judges whether the delay period has elapsed. If the delay period has expired, step 109 transfers to step 110 to cancel the fermenting function. At step 119 the temperature in the refrigerating chamber is adjusted at the predetermined fermenting temperature.

On the other hand, if the kimchi fermenting operation is not in the strong mode, step 106 moves to step 111 to judge whether the kimchi fermenting operation is the weak mode. If fermenting is weak, microcomputer $IC_1$ outputs a low level signal from its terminal $O_6$(step 112) and continues to allow kimchi to be fermented.

While the kimchi fermentor is in a fermentation mode, microcomputer $IC_1$ judges at step 114 whether a predetermined fermenting period, for example one hour or two hours, has elapsed. If the predetermined period has not ended, the number of gas bubbles from kimchi curing sensor 100 continue to be accumulated at step 115. But if the predetermined period at step 116 has expired, the number of gas bubbles counted so far is divided by the period (e.g., about two hours). Next step 116 moves to step 117 to judge whether the divided number of gas bubbles is larger than that produced in the previous predetermined time period. If the divided number is larger than the previously determined number, the divided number is stored (step 118). Otherwise step 117 goes on to step 120 to judge whether this is the first occurrence of a decrease in gas bubble production.

If this is the first occurrence of a decrease in gas bubble production, this time point is stored as the first peak point with respect to the production of gas bubbles (step 121). But if it is not the first, step 121 goes on to step 122 to judge whether it is the second peak point. If the number of gas bubbles reaches the second peak point, at step 123 this peak point is stored as the main peak. Step 123 moves into step 124 to judge whether the fermenting selection is the weak mode. If the kimchi fermenting mode is not set at the weak mode, step 124 moves to step 119. On the other hand, if kimchi fermenting mode is set at the weak mode, step 124 goes on step 127 to cancel the kimchi fermenting function, and moves to step 104 to adjust the temperature in the refrigerating chamber to a predetermined storage temperature.

If the number of gas bubbles is not judged to be the second peak point at step 122, step 122 goes on to step 125 to store the peak point as the third peak point. Next step 125 goes to step 126 to judge whether the fermenting function is the standard mode.

If the kimchi fermenting mode is not standard, step 126 is transferred to step 119. Otherwise, it is transferred to step 127, which cancels the kimchi fermenting function.

As described above, when the kimchi fermentor is turned on by applying power, microcomputer $IC_1$ judges the temperature in the refrigerating chamber by the signal received from temperature sensor TH, to maintain the temperature of the refrigerating chamber at the predetermined temperature, for example 25° C., suitable for kimchi fermentation according to the prior art method. If the temperature of the refrigerating chamber is higher than the predetermined temperature, the output $O_1$ of microcomputer $IC_1$ becomes high enough to turn transistor $Q_4$ on, so that compressor COMP is operated. If the temperature of the refrigerating chamber is lower than the predetermined temperature, the output $O_2$ of microcomputer $IC_1$ becomes high enough to turn transistor $Q_5$ on, so that heater H is operated. In either case, output $O_3$ also becomes high enough to turn transistor $Q_6$ on and operate the motor of fan F, so that the temperature of the refrigerating chamber is uniformly distributed in order to prevent parts of the kimchi from curing severely or the occurrence of undesirable tastes. That is, if the function of the kimchi fermentor is set to kimchi fermenting, a constant temperature suitable for kimchi fermenting, for example 25° C., is maintained. If the storage function is selected, a constant temperature suitable for storing kimchi, for example 5° C., is maintained.

Also, a kimchi curing degree may be selected among the degrees of strong, standard and weak to meet the user's taste using fermenting key $K_1$. From the initialization, if the user wants to use only the refrigerating function with the fermenting function being cancelled, he can cancel the fermenting function using fermenting cancelling key $K_2$. The function selection of kimchi fermentor is represented by light emitting diodes $L_1$–$L_4$, each of which is lit, respectively, when the outputs $O_4$–$O_7$ of microcomputer $IC_1$ become low and sink the current.

Accordingly, the present invention may be constructed as a home kimchi fermentor as well as an industrial kimchi fermentor. Also this kimchi fermentor can be used in places suitable for mass feeding, such as restaurants, hospitals, boarding houses and barracks, where mass production of kimchi is required. Furthermore, while the invention has been described with respect to kimchi fermentation, it is understood that by using the present invention various other naturally fermenting foodstuffs may also be automatically prepared.

What is claimed is:

1. A control system for a kimchi fermentor having a case for holding kimchi, an enclosure substantially containing said case, a compressor and evaporator for reducing the temperature within said enclosure, a heater for raising the temperature within said enclosure, and a fan for circulating a fluid within said enclosure comprising:

kimchi curing sensing means for producing a signal indicative of the extent of fermentation within said case;

temperature sensing means for producing a signal indicative of the temperature within said enclosure;

control means for generating control signals for controlling the temperature within said enclosure in response to said signal indicative of the extent of fermentation and said signal indicative of temperature; and operating means for activating said compressor, said heater, and said fan in response to said control signals.

2. The control system of claim 1, wherein said control means comprises a microcomputer and said operating means comprises a relay circuit means for providing operational power to the compressor in response to a first signal from the microcomputer, operational power to the fan in response to a second signal from the microcomputer, and operational power to the heater in response to a third signal from the microcomputer.

3. The control system of claim 2, wherein said relay circuit means comprises:

a first resistor connected between the microcomputer and a base of a first transistor, a second resistor connected from the base of the first transistor to ground, said first transistor having an emitter connected to ground and a collector connected to an input of a first relay means for providing operational power to said compressor, said first resistor receiving the first signal from the microcomputer;

a third resistor connected between the microcomputer and a base of a second transistor, a fourth resistor connected from the base of the second transistor to ground, said second transistor having an emitter connected to ground and a collector connected to an input of a second relay means for providing operational power to said heater, said third resistor receiving the second signal from the microcomputer; and a fifth resistor connected between the microcomputer and a base of a third transistor, a sixth resistor connected from the base of the third transistor to ground, said third transistor having an emitter connected to ground and a collector connected to an input of a third relay means for providing operational power to said fan, said fifth resistor receiving the third signal from the microcomputer.

4. The control system of claim 1, wherein said kimchi curing sensing means comprises: a photo interrupter, a first resistor connected between an output of the photo interrupter and a base of a transistor; a second resistor connected between the output of the photo interrupter and ground; said transistor having an emitter connected to ground and a collector connected to an input of said control means; and a third resistor connected between a voltage source and said collector, said collector of the transistor providing the sensing signal as pulses, said control means counting said pulses corresponding to the extent of fermentation of the kimchi.

5. The control system of claim 1, wherein said temperature sensing means comprises a first operational amplifier, a second operational amplifier, a resistor, and a thermistor, said first operational amplifier generating a predetermined reference voltage, said resistor being connected between an output of the first operational amplifier and a non-inverting input of the second operational amplifier, the thermistor being connected between ground and the non-inverting input of the second operational amplifier, an inverting input of the second operational amplifier being connected to an output of the second operational amplifier, said output of the second operational amplifier providing the temperature signal.

6. A kimchi fermentation control device, comprising:

means for generating a key input signal for triggering an initialization for adjusting fermentation;

means for displaying a state of fermentation; and processing means for:

determining whether a temperature appointed by a fermenting selection corresponding to said initialization is higher than a predetermined temperature;

determining a level of fermentation control from among a strong mode, a standard mode and a weak mode, when a fermenting function is selected by means of the key input signal, and causing said displaying means to display a representation of said level of fermentation control;

adjusting a temperature for a refrigerating chamber to said predetermined temperature;

providing a current value of a count by making said count of a number of bubbles produced by kimchi during fermentation while elapsed time during said fermentation is not more than a predetermined time;

determining whether said current value, when divided by said predetermined time, is larger than a previously value of said count divided by the predetermined time when the elapsed time has exceeded the predetermined time;

storing said current value when said current value divided by said predetermined time is not larger than the previously counted number divided by said predetermined time; and cancelling said fermenting function by comparing with said selected fermenting function a peak point of said occurrence of bubbles, and determining how many times said peak point occurs when a number of bubbles counted after occurrence of said peak point is not larger than a number of said bubbles counted before said predetermined time.

7. The device of claim 6, further comprised of:

container means for containing the kimchi producing said bubbles;

means controlled by said processing means, for changing progress of kimchi within said container means toward completion of said fermentation function; and means controlled by said processing means, for maintaining temperatures of kimchi within said container means.

8. The device of claim 6, further comprising:

fermentation curing sensing means for providing a first output signal indicative of a number of bubbles produced by kimchi during fermentation;

temperature sensing means for providing a second output signal indicative of a temperature of the refrigerating chamber;

means disposed in proximity to the refrigerating chamber for influencing temperatures within the refrigerating chamber;

control means for regulating operational enablement of said temperature influencing means; and said processing means adjusting a temperature of the refrigerating chamber to a predetermined temperature by controlling said enablement by said control means of said temperature influencing means, in dependence upon said first output signal, said second output signal, and said key input signal.

9. A food processing device, comprising:

bubble collecting means being in a form of a funnel, for accommodating bubbles;

bubble homogenium means including a tube having one end connected to receive said bubbles from said bubble collecting means;

measuring means for measuring a number of said bubbles traversing said tube, said measuring means comprising a photo-interrupter triggered by said bubbles received by said bubble homogenium means for producing a pulse signal having a triggering frequency indicative of the extent of fermentation of food generating said bubbles;

container means for containing food generating said bubbles during said fermentation;

means for changing progress of the food within said container means toward completion of said fermentation;

means for maintaining temperature of the food within said container means; and means coupled to said measuring means, for controlling said changing means and said maintaining means in dependence upon said triggering frequency.

10. The food processing device of claim 9, further comprising:

a temperature sensor producing an electrical signal indicative of temperatures ambient to the container means;

a fermenting barrel receiving said container means, provided with said temperature maintaining means, said temperature sensor, said measuring means;

said controlling means comprising a fermenting control system for generating control signals on a basis of input signals received from said temperature sensor and said triggering frequency; and relay operating means for controlling operations of means for heating and for cooling in accordance with said control signals.

11. The food processing device of claim 10, further comprising;

input means for enabling a user to generate a selection signal representative of a degree of the fermentation selected by the user; and said controlling means controls said accelerating means and said maintaining means in dependence upon said triggering frequency and said selection signal.

12. The food processing device of claim 11, further comprising:

temperature sensing means for providing an output signal indicative of temperature of food within said container means; and said controlling means controlling said accelerating means and said maintaining means in dependence upon said triggering frequency, said selection signal and said output signal.

13. The food processing device of claim 10, further comprising:

temperature sensing means for providing an output signal indicative of temperature of food within said container means; and said controlling means controlling said accelerating means and said maintaining means in dependence upon said triggering frequency and said output signal.

14. The food processing device of claim 9, further comprising:

input means for enabling a user to generate a selection signal representative of a degree of the fermentation selected by the use; and said controlling means controls said accelerating means and said maintaining means in dependence upon said triggering frequency and said selection signal.

15. The food processing device of claim 14, further comprising:

temperature sensing means for providing an output signal indicative of temperature of food within said container means; and said controlling means controlling said accelerating means and said maintaining means in dependence upon said triggering frequency, said selection signal and said output signal.

16. The food processing device of claim 9, further comprising:

temperature sensing means for providing an output signal indicative of temperature of food within said container means; and said controlling means controls said accelerating means and said maintaining means in dependence upon said triggering frequency and said output signal.

17. The food processing device of claim 9, further comprised of said controlling means:

performing an initialization for adjusting fermentation based upon a fermenting function selected by a key signal input by a user;

determining a level of fermentation control from among a strong mode, a standard mode and a weak mode, if a fermenting function is selected by means of the key signal, and generating a first output signal representing a state of fermentation after determining whether a temperature appointed by a fermenting selection is higher than a predetermined temperature;

generating a second output signal for adjusting a temperature of a refrigerating chamber surrounding said container means while providing a current value of a count obtained by counting a number of said bubbles produced by the food during fermentation if elapsed time during said fermentation is not more than a predetermined time;

determining whether said current value, when divided by the predetermined time, is larger than a predetermined number if the elapsed time has exceeded the predetermined time;

storing said current value if the counted number when divided by the predetermined time is not larger than the predetermined time, and controlling temperature of the refrigerating chamber during the predetermined time; and varying said fermenting function on a basis of a comparison between said selected fermenting function and a peak point of occurrence of bubbles from the food, and a determination of how many times said peak point occurs if the number of bubbles counted after occurrence of said peak point is not larger than the number of bubbles counted before expiration of the predetermined time.

18. The food processing device of claim 9, wherein said changing means comprises a heater and said maintaining means comprises a compressor, an evaporator, and a fan, said device further comprising:

an enclosed substantially containing said container means;

temperature sensing means for producing a first signal indicative of temperatures within said enclosure;

operating means for activating said compressor, said heater, and said fan in response to control signals; and said controlling means generating said control signals for controlling said temperatures within said enclosure in response to said first triggering frequency and said signal.

19. A food processing device, comprising:

fermentation curing sensing means for providing a first output signal indicative of the extent of fermentation of food within a fermentor;

means disposed in proximity to the fermentor for influencing temperatures of the food within the fermentor;

control means for regulating operational enablement of said temperature influencing means;

temperature sensing means for providing a second output signal indicative of said temperature of food within said fermentor;

input means for enabling a user to generate a key input signal representative of a degree of fermentation desired by the user; and processing means for controlling said enablement by said control means of said temperature influencing means, in dependence upon said first output signal, said second output signal, and said key input signal.

20. The food processing device of claim 19, wherein said means for influencing temperatures comprises means for extracting heat from a medium surrounding the fermentor, means for exhausting heat to the medium, and means for circulating the medium between the heat extracting means, the heat exhausting means, and the fermentor.

21. The food processing device of claim 20, comprising said processing means:

performing an initialization for adjusting said fermentation based on said key input signal;

determining a level of fermentation control from among a strong mode, a standard mode and a weak mode each providing a different relative degree of fermentation when a degree of fermentation is selected by means of said key input signal, and controlling said enablement to adjust a temperature of the fermentor to the predetermined temperature while providing a current counted number obtained by counting a number of bubbles produced by food within the fermentor during said fermentation while elapsed time during said fermentation is not more than a predetermined time;

determining whether the current counted number, when divided by the predetermined time, is larger than a previously counted number divided by the predetermined time when the elapsed time has exceeded the predetermined time;

storing the current counted number when the counted number divided by the predetermined time is not larger than the previously counted number divided by the predetermined time; and cancelling the degree of fermentation selected by comparing the degree of fermentation selected and the peak point of occurrence of bubbles from the food, and determining how many times the peak point occurs when the number of bubbles counted after occurrence of said peak point is not larger than the number of bubbles counted before the predetermined time.

22. The food processing device of claim 19, comprising said processing means:

performing an initialization for adjusting said fermentation based on said key input signal;

determining a level of fermentation control from among a strong mode, a standard mode and a weak mode each providing a different relative degree of fermentation when a degree of fermentation is selected by means of said key input signal, and controlling said enablement to adjust a temperature of the fermentor to the predetermined temperature while providing a currently counted number obtained by counting a number of bubbles produced by food within the fermentor during said fermentation while elapsed time during said fermentation is not more than a predetermined time;

determining whether the currently counted number, when divided by the predetermined time, is larger than a previously counted number divided by the predetermined time when the elapsed time has exceeded the predetermined time;

storing the currently counted number when the currently counted number divided by the predetermined time is not larger than the previously counted number divided by the predetermined time; and cancelling the degree of fermentation selected by comparing the degree of fermentation selected and the peak point of occurrence of bubbles from the food, and determining how many times the peak point occurs when the number of bubbles counted after occurrence of said peak point is not larger than the number of bubbles counted before the predetermined time.

23. A method of kimchi preparation, comprising the steps of:

selecting a kimchi fermentation function from among a strong mode, a middle mode and a weak mode;

measuring a temperature of a refrigerating chamber;

adjusting said measured temperature of the refrigerating chamber to a predetermined temperature;

counting a number of bubbles produced by kimchi fermentation during a predetermined time period;

dividing the number of bubbles by the predetermined time period;

determining whether the divided number is greater than a previous said divided number of bubbles of a previous said predetermined time period;

if the divided number of bubbles of the predetermined time period is larger than the previous divided number of bubbles of the previous predetermined time, storing the divided number of bubbles of the predetermined time period as the number of bubbles of the previous time period;

cancelling the kimchi fermentation function of the weak mode at a second occurrence of the divided number of bubbles of the predetermined time period being larger than the divided number of bubbles of the previous time period, said second occurrence corresponding to a second local maximum point of kimchi fermentation;

cancelling the kimchi fermentation function of the middle mode at a third occurrence of the divided number of bubbles of the predetermined time period being larger than the divided number of bubbles of the previous time period, said third occurrence corresponding to a third local maximum point of kimchi fermentation; and cancelling the kimchi fermentation function of the strong mode a predetermined delay period after said third occurrence.

24. The process of kimchi preparation of claim 23, further comprising:

a kimchi fermentor having a case for holding kimchi;

a refrigerating chamber substantially containing said case;

a compressor and evaporator for reducing the temperature within said refrigerating chamber;

a heater for raising the temperature within said refrigerating chamber;

a fan for circulating a fluid within said refrigerating chamber;

kimchi curing sensing means for producing a signal indicative of the number of bubbles produced by kimchi fermentation within said case;

temperature sensing means for producing a signal indicative of the temperature within said refrigerating chamber;

operating means for activating said compressor, said heater, and said fan in response to said control signals; and control means for performing said process steps by generating control signals for controlling the temperature within said refrigerating chamber in response to said signal indicative of the extent of fermentation and said signal indicative of temperature.

25. A process of kimchi preparation, comprising the steps of:

initiating kimchi fermentation in one of a strong mode, a standard mode and a weak mode;

adjusting a temperature of a refrigerating chamber to a predetermined temperature;

counting a number of bubbles produced by kimchi fermentation during a current time period;

determining whether the number of bubbles produced by kimchi fermentation during the current time period is greater than a number of bubbles produced by kimchi fermentation during a previous time period;

if the number of bubbles of the current time period is larger than the number of bubbles of the previous time period, then storing the number of bubbles of the current time period as the number of bubbles of the previous time period;

if the kimchi fermentation is occurring in the weak mode, then ending said kimchi preparation process upon a second occurrence of the number of bubbles of the current time period not being larger than the number of bubbles of the previous time period, said second occurrence corresponding to a second peak point of kimchi fermentation;

if the kimchi fermentation is occurring in the middle mode, then ending the kimchi preparation process upon a third occurrence of the number of bubbles of the current time period not being larger than the number of bubbles of the previous time period, said third occurrence corresponding to a third peak point of kimchi fermentation; and if kimchi fermentation is occurring in the strong mode, ending the kimchi fermentation process a predetermined delay period after said third occurrence.

26. The process of kimchi preparation of claim 25, further comprising:

a kimchi fermentor having a case for holding kimchi;

a refrigerating chamber substantially containing said case;

a compressor and evaporator for reducing the temperature within said refrigerating chamber;

a heater for raising the temperature within said refrigerating chamber;

a fan for circulating a fluid within said refrigerating chamber;

kimchi curing sensing means for producing a signal indicative of the number of bubbles produced by kimchi fermentation within said case;

temperature sensing means for producing a signal indicative of the temperature within said refrigerating chamber;

operating means for activating said compressor, said heater, and said fan in response to said control signals; and control means for performing said process steps by generating control signals for controlling the temperature within said refrigerating chamber in response to said signal indicative of the extent of fermentation and said signal indicative of temperature.

27. A method of kimchi preparation, comprising the steps of:

initiating kimchi fermentation by selecting one of a plurality of kimchi fermentation modes;

adjusting a temperature of a refrigerating chamber to a predetermined temperature;

counting a number of bubbles produced by kimchi fermentation during a current time period;

determining whether the number of bubbles produced by kimchi fermentation during the current time period is greater than a number of bubbles produced by kimchi fermentation during a previous time period;

if the number of bubbles of the current time period is not larger than the number of bubbles of the previous time period, then storing the number of bubbles of the current time period;

if the number of bubbles of the current time period is not larger than the number of bubbles of the previous time period, then determining a local maximum point of kimchi fermentation; and ending kimchi fermentation in response to a predetermined said local maximum point of kimchi fermentation.

28. The method of claim 27, wherein said ending step further comprises ending kimchi fermentation in response to the predetermined said local maximum point of kimchi fermentation and a predetermined delay time.

29. The process of kimchi preparation of claim 27, further comprising:

a kimchi fermentor having a case for holding kimchi;

a refrigerating chamber substantially containing said case;

a compressor and evaporator for reducing the temperature within said refrigerating chamber;

a heater for raising the temperature within said refrigerating chamber;

a fan for circulating a fluid within said refrigerating chamber;

kimchi curing sensing means for producing a signal indicative of the number of bubbles produced by kimchi fermentation within said case;

temperature sensing means for producing a signal indicative of the temperature within said refrigerating chamber;

operating means for activating said compressor, said heater, and said fan in response to said control signals; and control means for performing said process steps by generating control signals for controlling the temperature within said refrigerating chamber in response to said signal indicative of the extent of fermentation and said signal indicative of temperature.

30. A control system for a fermentation device containing food to be fermented comprising:

input means enabling a user to generate a key input signal representative of a degree of fermentation desired by the user; and processing means for:

adjusting a temperature within said device to a predetermined fermentation temperature;

accumulating a sensed number of bubbles produced by the food over a plurality of equivalent predetermined time periods;

identifying a plurality of peak points in said sensed number of bubbles by determining whether a first said number accumulated over a single predetermined period is greater than a sensed number of bubbles accumulated over an equivalent time period immediately preceding said predetermined time period; and adjusting a temperature within said device to a predetermined storage temperature when a peak point is identified corresponding to said key input signal from said input means.

31. The control system of claim 30, further comprising:

means disposed in proximity to the device for influencing temperatures of the food within the device;

fermentation curing sensing means for providing a first output signal indicative a number of bubbles produced by the food within the fermentation device;

temperature sensing means for providing a second output signal indicative of a temperature of food within the fermetation device;

control means for regulating operational enablement of said temperature influencing means in dependance on said processing means;

said processing means adjusting a temperature within the device by controlling said enablement by said control means of said temperature influencing means, in dependence upon said first output signal, said second output signal, and said key input signal.

32. The control system of claim 30, further comprising:

said input means enabling a user to generate one of a first, second, and third key input signals representative of a weak mode, a standard mode, and a strong mode, respectively, each providing a different relative degree of fermentation; and said processing means adjusting a temperature within said device to a predetermined storage temperature when a second peak point is identified following user generation of said first key input signal, when a third peak point is identified following user generation of said second key input signal, and after a predetermined delay when a third peak point is identified following user generation of said third key input signal.

* * * * *